United States Patent
Pekar et al.

(10) Patent No.: US 10,946,214 B2
(45) Date of Patent: *Mar. 16, 2021

(54) AUTOMATED ANATOMY DELINEATION FOR IMAGE GUIDED THERAPY PLANNING

(71) Applicant: KONINKLIJKE PHILIPS N.V., Eindhoven (NL)

(72) Inventors: Vladimir Pekar, Toronto (CA); Daniel Bystrov, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 849 days.

This patent is subject to a terminal disclaimer.

(21) Appl. No.: 15/638,914

(22) Filed: Jun. 30, 2017

(65) Prior Publication Data

US 2017/0296841 A1 Oct. 19, 2017

Related U.S. Application Data

(63) Continuation of application No. 13/260,735, filed as application No. PCT/IB2010/050893 on Mar. 2, 2010, now Pat. No. 9,724,538.

(Continued)

(51) Int. Cl.
*A61B 5/05* (2006.01)
*A61N 5/10* (2006.01)
(Continued)

(52) U.S. Cl.
CPC ............... *A61N 5/103* (2013.01); *G06T 7/12* (2017.01); *G06T 7/149* (2017.01); *G06T 7/174* (2017.01);
(Continued)

(58) Field of Classification Search
CPC . A61N 5/103; G06F 19/3481; G06T 2200/04; G06T 2207/10081;
(Continued)

(56) References Cited

U.S. PATENT DOCUMENTS

| 5,946,425 A | 8/1999 | Bove |
|---|---|---|
| 8,554,573 B2 | 10/2013 | Pekar |

(Continued)

FOREIGN PATENT DOCUMENTS

| WO | 2009/109874 | 9/2009 |
|---|---|---|
| WO | 2008/155738 | 12/2009 |

OTHER PUBLICATIONS

Fred L Bookstein: "Principal Warps: Thin-Plate Splines and the Decomposition of Deformations", IEEE Transactions on Pattern Analysis and Machine Intelligence, vol. 11, No. 6, Jun. 1989.

(Continued)

*Primary Examiner* — Christopher L Cook

(57) ABSTRACT

When delineating anatomical structures in a medical image of a patient for radiotherapy planning, a processor (18) detects landmarks (24) in a low-resolution image (e.g., MRI or low-dose CT) and maps the detected landmarks to reference landmarks (28) in a reference contour of the anatomical structure. The mapped landmarks facilitate adjusting the reference contour to fit the anatomical structure. The adjusted reference contour data is transformed and applied to a second image using a thin-plate spline, and the adjusted high-resolution image is used for radiotherapy planning.

20 Claims, 4 Drawing Sheets

Related U.S. Application Data

(60) Provisional application No. 61/165,923, filed on Apr. 2, 2009.

(51) Int. Cl.
| | | |
|---|---|---|
| *G16H 20/40* | (2018.01) | |
| *G16H 30/20* | (2018.01) | |
| *G06T 7/174* | (2017.01) | |
| *G06T 7/12* | (2017.01) | |
| *G06T 7/33* | (2017.01) | |
| *G06T 7/149* | (2017.01) | |
| *G16H 30/40* | (2018.01) | |

(52) U.S. Cl.
CPC .............. *G06T 7/33* (2017.01); *G16H 20/40* (2018.01); *G16H 30/20* (2018.01); *G16H 30/40* (2018.01); *G06T 2200/04* (2013.01); *G06T 2207/10081* (2013.01); *G06T 2207/30016* (2013.01)

(58) Field of Classification Search
CPC ....... G06T 2207/30016; G06T 2210/41; G06T 2219/2021; G06T 7/12; G06T 7/149; G06T 7/174; G06T 7/33; G16H 20/40; G16H 30/20
See application file for complete search history.

(56) References Cited

U.S. PATENT DOCUMENTS

| | | |
|---|---|---|
| 2007/0153969 A1 | 7/2007 | Maschke |
| 2008/0123921 A1 | 5/2008 | Gielen |
| 2008/0167547 A1 | 7/2008 | Bova |

OTHER PUBLICATIONS

Dawson, et al., "Advances in Image-Guided Radiation Therapy", 2007, Journal of Clinical Oncology; 25(8) 938-946.

Kessler., et al., "Image Fusion for Conformal Radiation Therapy", 2001, reprinted from: 3D Conformal Radiation Therapy and Intensity Modulated Radiation Therapy: Physics and Clinical Considerations; J.A. Purdy, et al., Eds.; Advanced Medical Publishing.

Maintz, et al., "A survey of medical image registration" 1998, Medical Image Analysis; 2(1)1-36.

Ntasis, et al., Real-Time Collaborative Environment for Radiation Treatment Planning Virtual Simulation; 2002; IEEE Trans. on Biomedical Engineering; 49(12)1444-1451.

Pekar, et al., "Automated Planning of Scan Geometries in Spine MRI Scans", 2007; Int. Conf. on Medical Image Computing and Computer-Assisted Intervention; vol. 10; Part 1:601-608.

Wang, et al., "Performance Evaluation of Automatic Anatomy Segmentation Algorithm on Repeat of Four-Dimensional Computed Tomography Images Using Deformable Image Registration Method", 2008; Int. J. Radiation Oncology Biol. Phys.: 72(1)210-219.

Young, et al., "Automated Planning of MRI Neuro Scans", 2006; Proc. of SPIE; vol. 6144.

AUTOMATED ANATOMY DELINEATION FOR IMAGE GUIDED THERAPY PLANNING

CROSS REFERENCE TO RELATED APPLICATIONS

This application is a continuation of U.S. application Ser. No. 13/260,735, filed Sep. 28, 2011 and since issued as U.S. Pat. No. 9,724,538 on Aug. 8, 2017, which is a national filing of PCT application serial no. PCT/IB2010/050893, filed Mar. 2, 2010, published as WO 2010/113050 A1 on Oct. 7, 2010, which claims the benefit of U.S. provisional application Ser. No. 61/165,923 filed Apr. 2, 2009, which is incorporated herein by reference.

DESCRIPTION

The present application finds particular utility in medical imaging systems. However, it will be appreciated that the described technique(s) may also find application in other types of imaging systems, other therapy planning systems, and/or other medical applications.

Delineation of anatomy is a prerequisite step in therapy planning, such as radiation treatment planning (RTP) and the like. The primary imaging modality typically used in RTP is computed tomography (CT). The use of magnetic resonance imaging (MRI) for RTP is recently getting attention, since this modality provides superior soft tissue contrast compared to CT.

Automated scan planning systems are currently commercially available for MR examinations. One example of such a system is Philips SmartExam™, where a low resolution scout image is acquired, automated recognition of patient-specific anatomical landmarks is carried out, and the orientation of slices in the diagnostic scan is estimated based on the identified landmarks and the landmark and orientation information recorded from previous acquisitions.

Automated anatomy delineation is a challenging task in both CT and MRI. CT images do not generally provide good soft tissue contrast, which makes reliable organ boundary discrimination difficult. MR data show much better soft tissue differentiation compared to CT and their use can be advantageous in therapy planning for achieving more precise delineations of the target and critical structures in certain applications. However, automated segmentation of MRI data is also difficult due various different contrasts used leading to non-reproducible gray value distribution.

There is an unmet need in the art for systems and methods that facilitate delineation of anatomical structures in image-guided therapy planning, using anatomical landmarks to transfer delineations used for therapy planning, and the like, thereby overcoming the deficiencies noted above.

SUMMARY

In accordance with one aspect, a system that facilitates delineating anatomical features in images used for image-guided therapy planning includes a processor that receives an initial image of an anatomical structure in a patient from an imaging device, and detects anatomical landmarks in the initial image. The processor additionally compares positions of the detected anatomical landmarks with reference landmarks in a reference contour corresponding to the anatomical structure, maps the detected anatomical landmarks to the reference landmarks, and adjusts the reference contour to the anatomical structure based on the mapped landmark pairs. The processor also adjusts a contour of the anatomical structure in a high-resolution image of the anatomical structure using the adjusted reference contour, stores an adjusted high-resolution image to a memory, and provides the adjusted high-resolution image to a therapy planning component.

In accordance with another aspect, a method of delineating anatomical features in images used for image-guided therapy planning includes detecting anatomical landmarks in an initiated image, and comparing positions of the detected anatomical landmarks with reference landmarks in a reference contour corresponding to the anatomical structure. The method further includes mapping the detected anatomical landmarks to the reference landmarks, and adjusting the reference contour to the anatomical structure based on the mapped landmark pairs. The method additionally includes adjusting a contour of the anatomical structure in a high-resolution image using the adjusted reference contour, and generating a therapy plan based at least in part on the adjusted high-resolution image.

In accordance with another aspect, a method of generating a radiotherapy plan for a patient includes generating a low-resolution image of the patient using at least one of a magnetic resonance imaging (MRI) device and a computed tomography (CT) scanner, and detecting landmarks on an anatomical structure in low-resolution image. The method further includes mapping the detected landmarks to reference landmarks in a reference contour stored in a memory, and employing spline interpolation or approximation to adjust the reference contour to fit a contour of the anatomical structure using the mapped landmarks. The method additionally includes applying the adjusted reference contour to a high-resolution image of the anatomical structure to adjust the high-resolution image, and generating a radiotherapy plan based at least in part on the adjusted high-resolution image.

One advantage is that image quality for therapy planning is improved.

Another advantage resides in reduced image adaptation time.

Still further advantages of the subject innovation will be appreciated by those of ordinary skill in the art upon reading and understand the following detailed description.

BRIEF DESCRIPTION OF THE DRAWINGS

The drawings are only for purposes of illustrating various aspects and are not to be construed as limiting.

DETAILED DESCRIPTION

In accordance with various features presented herein, systems and methods are described that facilitate delineation of anatomical structures in image-guided therapy planning. The described framework is based on patient-specific landmark automatically recognized by the scan planning software (e.g. Philips SmartExam™ MR scan planning systems). These landmarks are used to support automated anatomy delineation as well as propagation of delineations in the context of adaptive treatment planning.

Analogously, automated CT scan planning is performed by detecting reproducible landmarks in low-dose scout scans. The detected landmarks in the scout images are used to guide the automated segmentation algorithms by yielding close initializations and also to propagate delineations to the follow-up images by landmark-based non-rigid registration.

The herein-described systems and methods solve the problem of providing reproducible anatomical point landmarks for therapy planning. For instance, automated scan planning algorithms, such as Philips SmartExam™, typically operate on 3-D standardized low-resolution scout images and are able to reliably recognize the target anatomy in the form of reproducible anatomical point landmarks. Thus, spatial information about the underlying anatomy obtained from the scout image is transferred to the full-resolution scan, regardless of the contrast, and used to support automated delineation.

Figure 1:
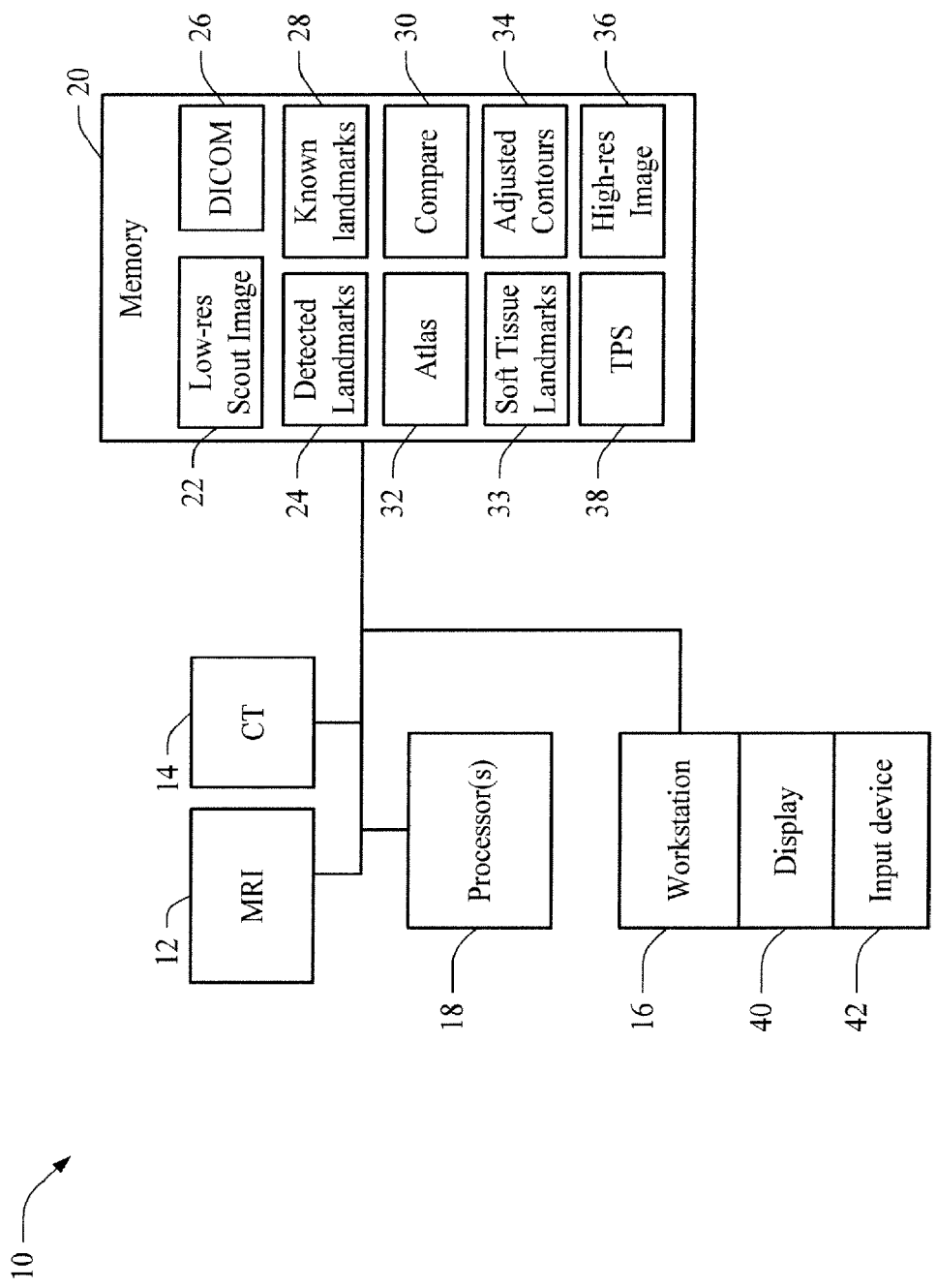
FIG. 1 illustrates a system that facilitates propagating contours or delineations from medical images to high-resolution images used for therapy planning.

FIG. 1 illustrates a system 10 that facilitates propagating contours or delineations from medical images to high-resolution images used for therapy planning. For instance, the system 10 can be employed with one or more radiotherapy planning workstations in a combination with a SmartExam™-enabled MR scanner. Also, the method of propagating contours or treatment plans can be used with CT-images with corresponding landmarks in 3-D low-dose CT scout images. According to other features, the system 10 employs multimodality systems (e.g., combined CT-MR, as well as MR and/or CT combined with nuclear imaging systems such as a positron emission tomography (PET) scanner, a single-photon emission computed tomography (SPECT scanner, etc.)

The system 10 includes one or both of an MRI device 12 and a CT scanner 14, which are coupled to a workstation 16, a processor 18, and a memory 20. The processor can be part of the workstation 16 or can be a resource shared by a plurality of workstations. The memory stores, and the processor executes, computer executable instructions for carrying out the various tasks and performing the various methods described herein.

In one embodiment, the CT scanner 14 generates a 3-D low-dose scout image 22, and the processor 18 automatically detects a reproducible set of landmarks 24 in the low-dose scout image. The detected landmarks are exported (e.g., using a digital imaging communication in medicine (DICOM) data exchange protocol 26 or the like) to the processor for comparison to known landmarks 28 stored in the memory for one or more contours. The processor executes a comparison algorithm 30 to compare the detected landmarks to the known landmarks, and retrieves one or more body contours from an atlas 32 stored in the memory. The processor transforms the contours using the detected landmarks, thereby adjusting one or more pre-generated contours by mapping the detected landmarks to the known landmarks for the contour(s). For example, the processor determines a transform that transforms the pilot image landmarks 24 into locations that overlay the atlas landmarks 28. The inverse of this determined transform can be applied to the atlas contour to transform it into an adjusted contour 34 in patient space.

In another embodiment, the MRI device 12 generates a low-resolution scout image 22, and the processor 18 automatically detects the reproducible set of landmarks 24 in the low-resolution scout image. The detected landmarks are exported (e.g., using a DICOM data exchange protocol 26 or the like) to the processor for comparison to known soft tissue landmarks 33 stored in the memory for one or more contours. The processor executes the comparison algorithm 30 to compare the detected landmarks 24 to the known landmarks 28, and retrieves one or more body contours from the atlas 32 stored in the memory. The processor transforms the atlas contours using the detected landmarks 24, thereby adjusting one or more pre-generated atlas contours into the adjusted contours 34 by mapping the detected landmarks to the known landmarks for the contour(s).

In either scenario (e.g., CT or MRI), the atlas is transformed to the new, patient-specific data set derived from the low-dose scout image. That is, the processor executes a transform to move the adjusted contours 34 to a high resolution image 36 that is used for RTP. The adjusted contours or delineations are additionally used in follow-up images of the same patient in order to monitor therapy progress and facilitate adaptive therapy planning.

In one embodiment, the processor 18 employs one or more thin-plate splines 38 to transform the contours, although the described systems and methods are not limited thereto. An example of a thin-plate spline technique is described in F. L. Bookstein: Principal warps: Thin-plate splines and the decomposition of deformations. *IEEE Trans. Pattern. Anal. Mach Intell.* 11: 567-586, 1989.

In another embodiment, the workstation 16 includes a display 40 on which one or more of the low-resolution image 22, the high-resolution image 36, the detected landmarks 24, the known landmarks 28, the contours in the atlas 32, and/or the adjusted contours 34 are presented to a user at various stages of the described methods and processes. The workstation additionally includes an input device 42 (e.g., a mouse, keyboard, directional pad, stylus, etc.) by which a user inputs data and/or instructions to the workstation, adjusts landmarks, and the like.

Figure 3:
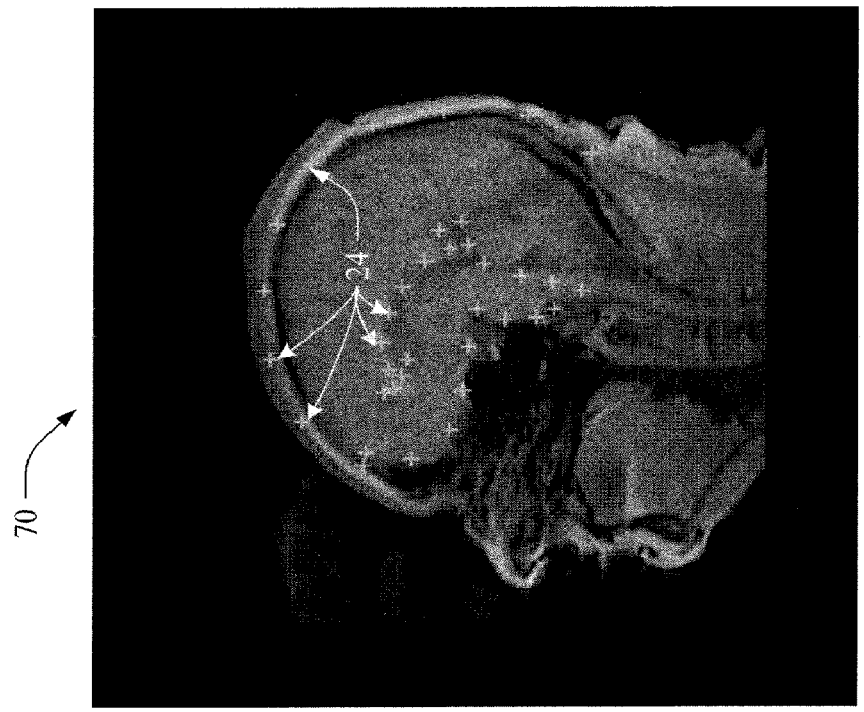
FIG. 3 illustrates another screen shot of automated delineation of brain images generated using an MRI device, which may be displayed to a user on the display.
Figure 2:
FIG. 2 illustrates a screen shot of automated delineation of brain images generated using an MRI device, which may be displayed to a user on the display.

With continues reference to FIG. 1, FIGS. 2 and 3 illustrate screen shots 60 and 70, respectively, of automated delineation of brain images generated using an MRI device, which may be displayed to a user on the display 40. FIG. 2 illustrates a plurality of the known or reference landmarks 28, and FIG. 3 shows a plurality of detected landmarks 24. The system 10 of FIG. 1 is employed, for example, to support delineation of structures-at-risk, as well as to propagate complete delineations from a primary dataset to the follow-up images automatically.

Anatomy recognition software such as SmartExam™ is available for brain examinations in many types of Philips MR scanners, as discussed in Young et al.: Automated Planning of MRI Neuro Scans. Proc. of SPIE Medical Imaging, San Diego, Calif., USA (2006) 61441M-1-61441M-8. As an output of the anatomy recognition software, the set of reproducible anatomical landmarks 24 is identified or detected. The positions of the landmarks can be exported using standard DICOM data exchange protocol 26 and used by an anatomy delineation module (not shown) of the radiation therapy planning workstation 16 or by any standalone automated delineation software.

According to one embodiment, a user manually delineates the structures of interest in a reference dataset, for which the landmark positions are available. These known landmarks 28 are then registered with the detected landmarks 24 in the specific patient dataset, e.g. using thin-plate splines or the like. The resulting transformation is applied to the anatomical structures in the reference dataset to transfer them to the patient dataset (e.g., in a high-resolution patient image or the like). The user can use further automated methods to obtain increased accuracy or to manually fine-tune the transferred delineations to fit them to the patient image.

In a related embodiment, the delineations are propagated to follow-up images of the same patient in the context of adaptive radiotherapy planning. Again, the detected landmarks 24 in the primary dataset are registered with known landmarks 28 in a reference data set, and the resulting transformation is applied to the available delineation in the primary patient image. Since there is much less anatomical variability present in this case, the method requires only minimum manual adjustments given optimal coverage of the region of interest by the landmarks.

Figure 4:
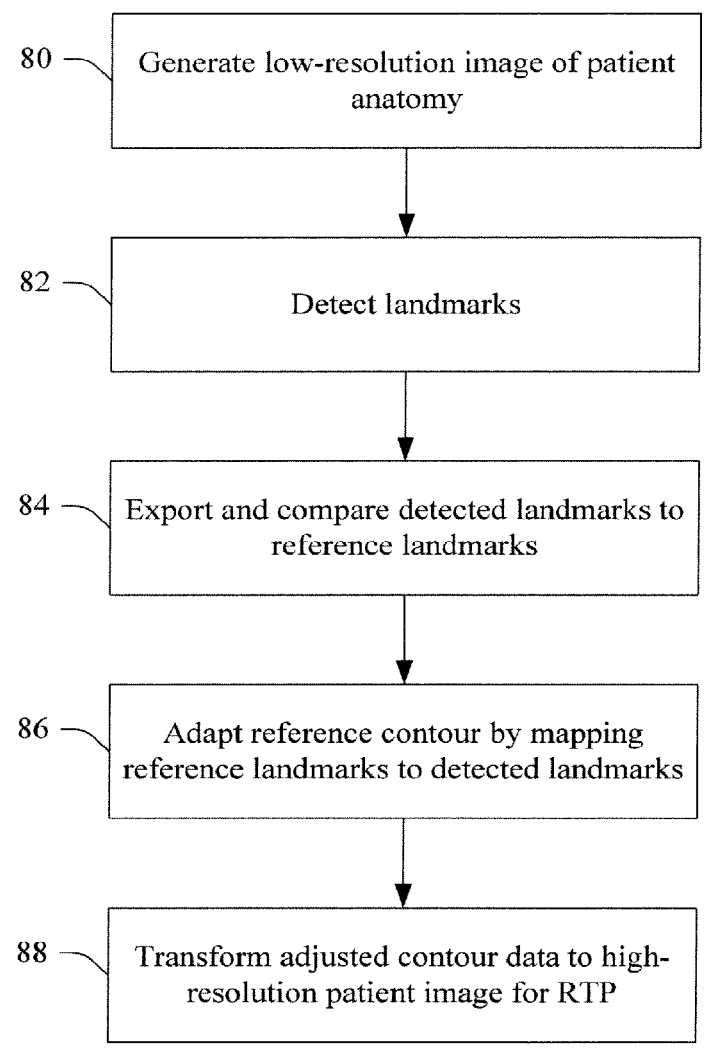
FIG. 4 illustrates a method of delineating patient anatomical structures to define contours in a patient image for image guided patient therapy, in accordance with one or more aspects described herein.

FIG. 4 illustrates a method of delineating patient anatomical structures to define contours in a patient image for image guided patient therapy, in accordance with one or more aspects described herein. At 80, a low-resolution image of the patient or a portion of the patient is generated. In one embodiment, the image is a low-dose CT image. In another embodiment, the image is a low-resolution MR image. At 82, landmarks in the patient image are detected. At 84, the detected landmarks 24 are exported (e.g., using a DICOM data transfer protocol 26 or the like) and compared to known landmarks 26 for contours in a pre-generated atlas 32 of anatomical structures. If the initial patient image is a low-dose CT image, then the detected landmarks are compared to known hard-structure (e.g., bone, etc.) landmarks. If the initial patient image is a low-resolution MR image, then the detected landmarks are compared to soft tissue reference landmarks.

At 86, a reference contour including the reference landmarks is retrieved from an atlas of reference contours and adjusted (e.g., warped, morphed, conformed) to the patient image by mapping the reference landmarks 28 to the detected landmarks 24. The adjusted contour may be stored to memory for recall at a later time. At 88, the adjusted contour is transformed (e.g., using a thin-plate spline or some other suitable interpolation technique) to fit a high-resolution patient image, which is adapted for use in a therapy planning procedure, such as a radiotherapy planning procedure. A user may additionally fine-tune the adapted contour using known techniques.

It will be appreciated that the high-resolution image may be generated using any imaging modality, such as CT, MRI, positron emission tomography (PET) single photon emission computed tomography (SPECT), x-ray, variants of the foregoing, etc. In such scenarios, the processor provides a contour with modality-specific landmarks for mapping to the detected landmarks. The atlas 32 has both hard-structure landmarks, soft-tissue landmarks, PET landmarks, SPECT landmarks, x-ray landmarks, and the like, so that any or all of CT, MR, PET, SPECT, x-ray, and other images and landmarks can be mapped to or registered with the atlas contours.

In another embodiment, in addition to or in place of the atlas of reference contours, a plurality of initial landmarks is obtained for a patient during a first imaging session. The initial landmarks are then used for comparison in subsequent imaging sessions to evaluate therapy progress and the like.

Figure 5:
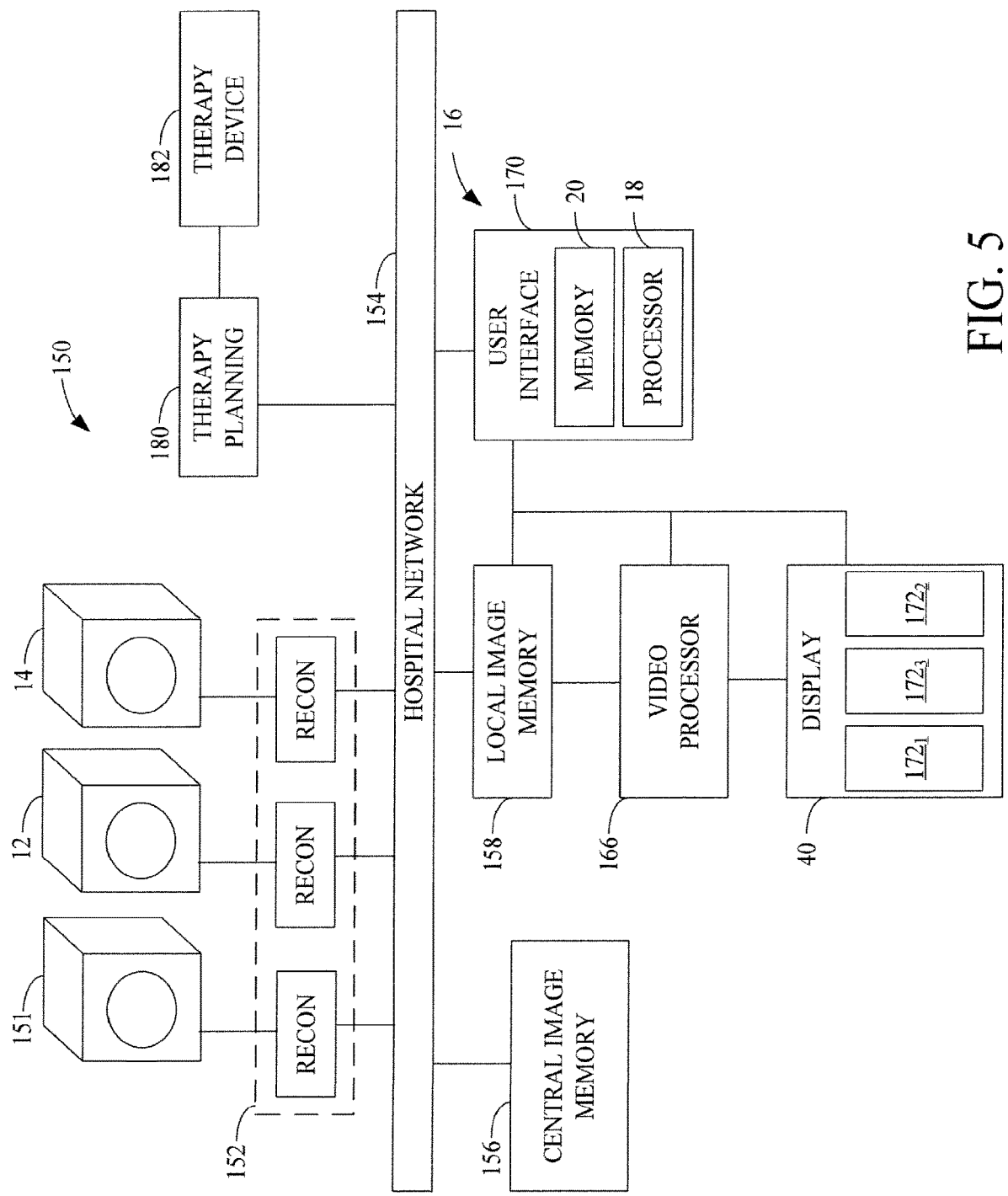
FIG. 5 illustrates an exemplary hospital system that includes a plurality of imaging devices, such as an MR imaging device, a CT scanner, a nuclear (e.g., PET or SPECT) scanner, or the like, which generate imaging data that are reconstructed by individual or shared reconstruction processors to generate 3D image representations.

With reference to FIG. 5, an exemplary hospital system 150 may include a plurality of imaging devices, such as an MR imaging device 12, a CT scanner 14, a nuclear (e.g., PET or SPECT) scanner 151, combinations of the foregoing (e.g., multimodality systems) or the like, which generate imaging data that are reconstructed by individual or shared reconstruction processors 152 to generate 3D image representations. The image representations are communicated over a network 154 to a central memory 156 or a local memory 158.

At a workstation 16 connected with the network, an operator uses user interface 170 to move a selected item (e.g., a low resolution 3D image or contour, etc.) to or between the central memory 156 and the local memory 158. A video processor 166 displays the selected item in a first viewport $172_1$, of a display 40. A patient image (e.g., high resolution image generated by one of the MR imager 12, the CT scanner 14, and the nuclear scanner 151) is displayed in a second viewport $172_2$. A third view port $172_3$ can display an overlay of the adjusted contour and the high-resolution image. For example, a user can be permitted to register landmarks detected in a low-resolution (e.g., CT or MR) image of the patient to reference landmarks in a reference contour selected form an atlas to conform the reference contour to the patient anatomy. For instance, the operator, through the interface 170, selects the reference landmarks in the reference contour (e.g., using a mouse, stylus, or other suitable user input device) that correspond to detected landmarks in the low-resolution image. Alternately, the reference and detected landmarks can be aligned automatically by a program executed by the processors 18 and/or 166, which is stored in the memory 20. The processor 18 (FIG. 1) in the user interface 170 then performs a warping or morphing algorithm to conform the shape of the reference contour to the shape of the patient's anatomy using the aligned landmarks. The processor 18 additionally performs a transform (e.g., using thin plate splines or some other suitable interpolation technique) to map the adjusted or conformed contour to the high-resolution image of the patient.

Once the high-resolution image includes the adjusted contour information, it is provided to a therapy planning component 180 for use in therapy planning (e.g., radiotherapy planning, ultrasound therapy planning, physical therapy planning, brachytherapy planning, high-intensity focused ultrasound (HIFU) MRI-guided therapy, particle-beam planning, ablation planning, etc.). A therapy device 182 is optionally coupled to the therapy planning device 180 for executing one or more therapy plans generated thereby.

In another embodiment, the overlay displayed in viewport $172_3$ is adjustable to weight the low-resolution image and/or contour relative to the high-resolution image, or vice versa. For instance a slider bar or knob (not shown), which may be mechanical or presented on the display 168 and manipulated with an input device, may be adjusted to vary the weight of the image in viewports $172_1$ and $172_2$. In one example, an operator can adjust the image in viewport $172_3$ from purely high-resolution image data (shown in viewport $172_2$), through multiple and/or continuous combinations of high-resolution and low-resolution image data, to purely low-resolution image data (shown in viewport $172_1$). For instance, a ratio of high-resolution image data to low-resolution image data can be discretely or continuously adjusted from 0:1 to 1:0. As another option, the high-resolution image data can be displayed in grayscale and the low-resolution image data can be colorized, or vice versa.

Once a user has downloaded and/or installed an atlas or contour library to the central memory 156, the atlas can be accessed via the network to facilitate contour adjustment transformation to the high-resolution image, and the like as described herein. According to this example, multiple workstations or user interfaces can access the contour library or atlas as need for specific patients or imaging sessions for various therapy planning procedures.

Having thus described the preferred embodiments, the invention is now claimed to be:

1. A system that facilitates delineating anatomical features in images used for image-guided therapy planning, including:
   an imaging device;
   a therapy planning processor; and
   an electronic processor programmed to:
      map anatomical landmarks detected in an initial image received from the imaging device to reference landmarks in a reference contour corresponding to the anatomical structure;
      adjust the reference contour to the anatomical structure based on mapped landmark pairs;
      adjust a contour of the anatomical structure in a second image, received from the imaging device, of the anatomical structure using the adjusted reference contour; and
      provide the adjusted second image to the therapy planning processor.

2. The system according to claim 1, wherein the reference contour is adjusted using a thin-plate spline.

3. The system according to claim 1, wherein the initial image is a low-dose computerized tomography (CT) image generated by a CT scanner.

4. The system according to claim 3, wherein the detected landmarks are hard-tissue landmarks.

5. The system according to claim 1, wherein the initial image is a low-resolution magnetic resonance (MR) image generated by an MR imaging (MRI) device.

6. The system according to claim 5, wherein the detected landmarks are soft-tissue landmarks.

7. The system according to claim 1, wherein the detected landmark position information is exported using a DICOM data transfer protocol.

8. The system according to claim 1, wherein the therapy planning processor is programmed to generate at least one of a radiotherapy plan, an ultrasound therapy plan, a particle therapy plan, an ablation therapy plan, and a physical therapy plan based at least in part on information contained in the adjusted second image.

9. The system according to claim 1, wherein the initial image and the second image are generated using different imaging modalities.

10. The system according to claim 9, wherein the initial image is generated using at least one of a computed tomography (CT) scanner and a magnetic resonance imaging (MRI) device, and wherein the second image is generated using at least one of the CT scanner, the MRI device, and a nuclear imaging device.

11. A method of delineating anatomical features in images used for image-guided therapy planning, including, with at least one computer processor:
   mapping detected anatomical landmarks detected in an initial image to reference landmarks in a reference contour corresponding to the anatomical structure;
   adjusting the reference contour to the anatomical structure based on the mapped landmark pairs;
   adjusting a contour of the anatomical structure in a second image using the adjusted reference contour; and
   generating a therapy plan based at least in part on the adjusted second image.

12. The method according to claim 11, further including at least one of:
   displaying at least one of the initial image and the second image on a display;
   storing at least one of the initial image and the second image to a memory; and
   storing the therapy plan to the memory.

13. The method according to claim 11, further including: adjusting the reference contour using a thin-plate spline.

14. The method according to claim 11, further including: generating the initial image with a CT scanner, wherein the detected landmarks are soft-tissue landmarks.

15. The method according to claim 11, further including: generating the initial image with an MRI device, wherein the detected landmarks are soft-tissue landmarks.

16. The method according to claim 11, further including: generating at least one of a radiotherapy plan, an ultrasound plan, a particle beam therapy plan, an ablation therapy plan, and a physical therapy plan based at least in part on information contained in the adjusted second image.

17. A non-transitory computer-readable medium carrying a computer program that controls one or more computers to perform the method according to claim 11.

18. A therapy-planning workstation including a processor programmed to perform the method according to claim 11.

19. A non-transitory computer-readable medium that stores computer-executable instructions for generating a therapy plan for a patient, for execution by a processor, the instructions including:
   mapping detected landmarks in a low-resolution image of the patient using at least one of a magnetic resonance imagine (MRI) device and a computed tomography (CT) scanner to reference landmarks in a reference contour stored in a memory;
   employing one or more thin-plate splines to adjust the reference contour to fit a contour of the anatomical structure using the mapped landmarks;
   applying the adjusted reference contour to a second image of the anatomical structure to adjust the second image; and
   generating a radiotherapy plan based at least in part on the adjusted second image.

20. The non-transitory computer-readable medium according to claim 19, the instructions further comprising:
   generating the second image using at least one of the CT scanner, the MRI device, and a nuclear scanner;
   wherein the second image is generated using a different imaging modality than the low-resolution image.

* * * * *